US007037907B1

(12) United States Patent
Stewart et al.

(10) Patent No.: US 7,037,907 B1
(45) Date of Patent: May 2, 2006

(54) ESTRADIOL CONJUGATES AND USES THEREOF (75) Inventors: Alastair George Stewart, North Balwyn (AU); David James McAllister, McKinnon (AU); Maree Patricia Collis, Prahran (AU); Alan Duncan Robertson, South Melbourne (AU)

(73) Assignee: The University of Melbourne, Parkville (AU)

( * ) Notice: Subject to any disclaimer, the term of this patent is extended or adjusted under 35 U.S.C. 154(b) by 0 days.

(21) Appl. No.: 10/110,647

(22) PCT Filed: Oct. 13, 2000

(86) PCT No.: PCT/AU00/01244

§ 371 (c)(1),
(2), (4) Date: Apr. 12, 2002

(87) PCT Pub. No.: WO97/11374

PCT Pub. Date: Mar. 27, 1997

(30) Foreign Application Priority Data

Oct. 14, 1999 (AU) .................................... PQ3425

(51) Int. Cl.
*A61K 31/56* (2006.01)
*C07J 1/00* (2006.01)
(52) U.S. Cl. ..................... 514/170; 514/169; 514/177; 514/178; 514/182; 514/171; 552/614; 552/627; 552/515; 552/553; 552/554
(58) Field of Classification Search .................... None
See application file for complete search history.

(56) References Cited

U.S. PATENT DOCUMENTS

| 5,739,302 | A | * | 4/1998 | Suzuki et al. .................. 536/5 |
| 5,792,757 | A | * | 8/1998 | Jennings-White et al. .. 514/170 |
| 6,051,726 | A | * | 4/2000 | Sachdeva et al. ........... 552/614 |
| 6,136,992 | A | | 10/2000 | Ram et al. |
| 6,281,205 | B1 | * | 8/2001 | Tanabe et al. ............... 514/176 |
| 6,352,980 | B1 | * | 3/2002 | Berliner et al. ............. 514/169 |
| 6,455,517 | B1 | * | 9/2002 | Tanabe et al. ............... 514/182 |
| 6,660,726 | B1 | * | 12/2003 | Hill et al. .................... 514/178 |
| 2002/0002294 | A1 | | 1/2002 | D'Amato et al. .............. 552/9 |

FOREIGN PATENT DOCUMENTS

WO   WO 95/04535   2/1995

OTHER PUBLICATIONS

Poirier, Donald et al., Molecular and Cellular Endocrinology 171, (2001), 119-128).*
Watanabe et al., Preperation and high-performance liquid chromatographic determination of guaiacol estrogen 17beta-conjugates, 1982, Chemical & Pharmaceutical Bulletin, 30(9), 3231-8, AN 1983:72528 HCAPLUS, DN 98:72528.*
Spiegelhalder et al., Mass-spectrometry of steroid glucoronides, 1976, Journal of Steroid Biochemistry, 7(10), 749-56, AN 1977:73062 HCAPLUS, DN 86:73062.*
Roehle et al., Synthesis of glucuronides of 2-hydroxylated estrogens and their methyl ethers, 1974, Hoppe-Seyler's Zeitschrifuer Physiologische Chemie, 355(4), 490-4, AN 1974:404163 HCAPLUS, DN 81:4163.*
Chemical Abstract 124:4208 & Bunseki Kagaku, 1995, vol. 44(10), pp. 793-796, K. Takanashi et al., "HPLC Separation of Ring D-Conjugated Estrogens."
Chemical Abstract 90:121859 & Chem. Pharm. Bull., 1978, vol. 26(11), pp. 3567-3571, A. Nakagawa et al., "Clinical Analysis on Steroids. Part V. Synthesis of 2,3,17.beta.-trihydroxyestra-1,3,5(10)-trien-6-one and its Related Compounds."
Chemical Abstract 97:163313 & Hoppe-Seyler's Z. Physiol. Chem., 1982, vol. 363(7), pp. 737-744, D. Berg et al., "Synthesis of Immunogenic C-6 Derivatives of 2-methoxyestrone and 2-methoxy-17.beta.-estrodiol and Characterization of the Corresponding Antiserums."
Chemical Abstract 73:116788 & J. Chromatgr., 1970, vol. 50(3), pp. 400-404, T. Nambara et al., "Analytical Chemical Studies on Steroids. XXXVII. Gas Chromatography of 2,3-Oxygenated Estratrienes."
Chemical Abstract 116:207984 & Biochem. Pharmacol., 1992, vol. 43(5), pp. 985-994, P. Morgan et al., "The Metabolism of 2- and 4-fluoro-17.beta.-estradiol in the Rat and its Implications for Estrogen Carcinogensis."
Höller et al., "Simultaneous Perfusion of [4-$^{14}$C]oestriol and [6,9-$^{3}$H$_2$]oestriol 16α-Monoglucuronide Through the Isolated Rat Liver," *Acta Endocrinol.* 100:57-62 (1982).
Nambara et al., "Syntheses of Methoxyestrogen Glucuronide Acetate-Methyl Esters," *Chem. Pharm. Bull.* 24:421-426 (1976).
Nambara et al., "Biliary Conjugated Metabolites of Estriol in the Rat," *Chem. Pharm. Bull.* 25:942-948 (1977).
Ohkubo et al., "Synthesis of 2-Hydroxyestriol Monoglucuronides and Monosulfates," *Steroids* 55:128-132 (1990).
Röhle et al., "Synthesis of Glucuronides of 2-Hydroxylated Oestrogens and their Methyl Ethers," *Hoppe-Seyler's Z. Physiol. Chem.* 355:490-494 (1974).
Spiegelhalder et al., "Mass-Spectrometry of Steroid Glucuronides," *J. Steroid Biochem.* 7:749-756 (1976).
Stalford et al., "The Metabolism of 16-Fluoroestradiols in vivo: Chemical Strategies for Restricting the Oxidative Biotransformations of an Estrogen-Receptor Imaging Agent," *Steroids* 62:750-761 (1997).

(Continued)

*Primary Examiner*—Sabiha Qazi
(74) *Attorney, Agent, or Firm*—Klarquist Sparkman, LLP (57) ABSTRACT

A conjugated prodrug of an estradiol compound conjugated to a biological activity modifying agent.

2 Claims, 6 Drawing Sheets

OTHER PUBLICATIONS

Watanabe et al., "Preparation and High-Performance Liquid Chromatographic Determination of Guaiacol Estrogen 17β-Conjugates: The Enzymatic O-Methylation Products of 2-Hydroxyestradiol 17β-Conjugates," *Chem. Pharm. Bull.* *30*:3231-3238 (1982).

* cited by examiner

FIGURE 1

FIGURE 2

Figure 3:
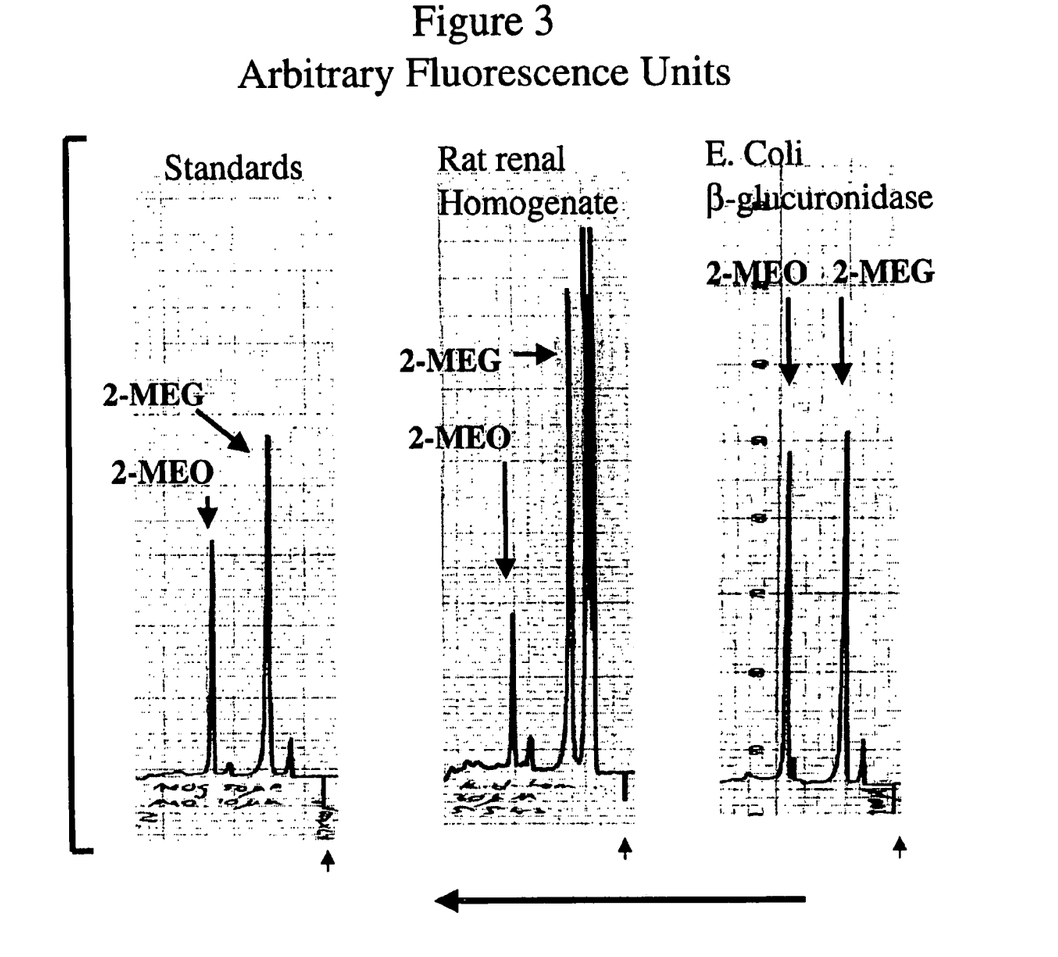

Figure 3
Arbitrary Fluorescence Units

Figure 4:
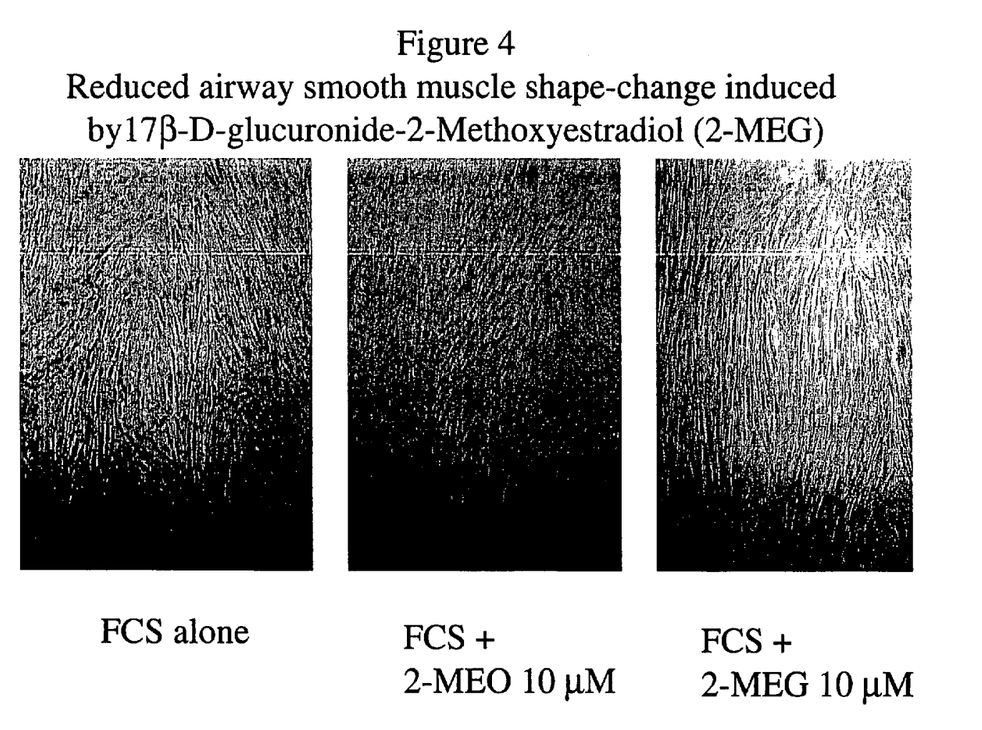

Figure 4
Reduced airway smooth muscle shape-change induced by17β-D-glucuronide-2-Methoxyestradiol (2-MEG)

FCS alone    FCS + 2-MEO 10 μM    FCS + 2-MEG 10 μM

Figure 6:
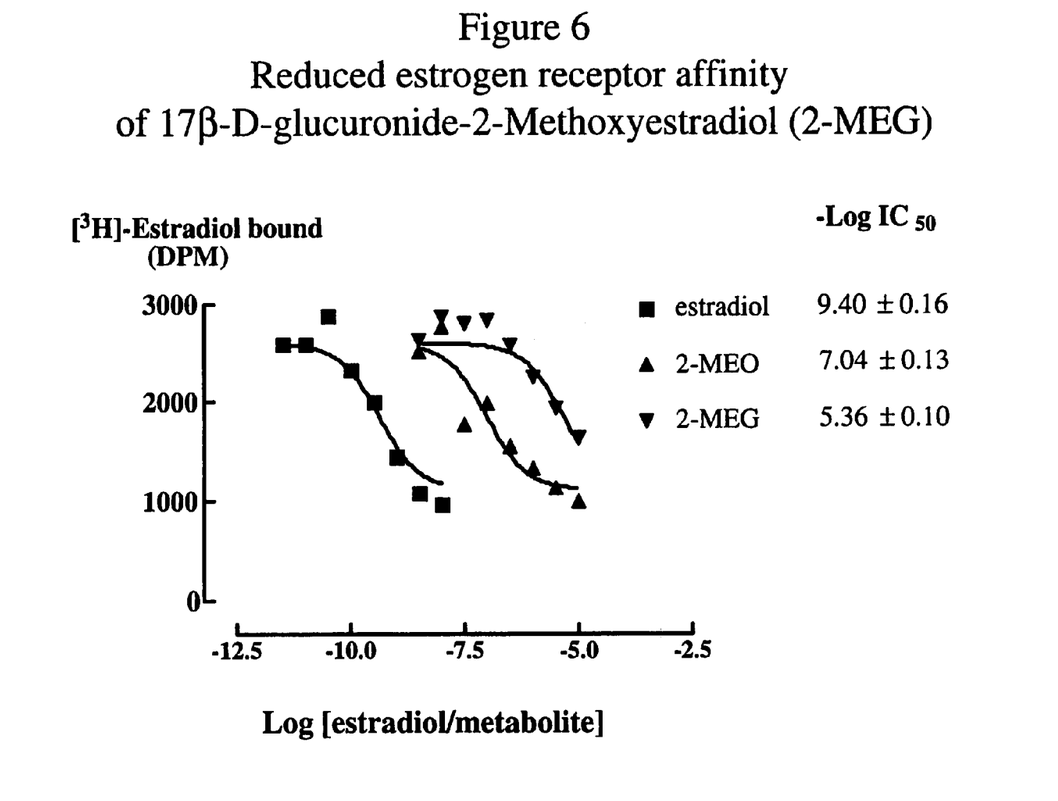

Figure 6
Reduced estrogen receptor affinity
of 17β-D-glucuronide-2-Methoxyestradiol (2-MEG)

ESTRADIOL CONJUGATES AND USES THEREOF

CROSS-REFERENCE TO RELATED APPLICATIONS

This is a § 371 national stage of PCT/AU00/01244, filed Oct. 13, 2000, which in turn claims the benefit of Australian Application No. PQ 3425 filed Oct. 14, 1999.

The present invention relates to conjugated prodrugs and uses thereof. More particularly, the invention relates to conjugates of estradiol compounds such as 2-methoxyestradiol and functionally active analogues and derivatives thereof, and the use of such conjugates in the prophylaxis or treatment of conditions associated with enhanced angiogenesis or accelerated cell division, such as cancer, and inflammatory conditions such as asthma and rheumatoid arthritis and hyperproliferative skin disorders including psoriasis. The invention also relates to compositions including the prodrugs of the present invention and methods of synthesizing the prodrugs.

Angiogenesis is crucial for the growth of solid tumors. Without angiogenesis tumour growth is limited to a microscopic size as a result of the limited distances that oxygen and other nutrients may diffuse. Solid tumors produce angiogenic factors, such as vascular endothelial growth factor (VEGF) and basic fibroblast growth factor (bFGF), at an early point in development. VEGF is considered to play a more significant role in the initiation of tumour neovascularisation, whereas basic Fibroblast growth factor (bFGF) is considered important in the maintenance of the angiogenic response. There is unequivocal evidence that targeting angiogenesis even after activation of the angiogenic switch can reduce further tumour growth. A further and unanticipated effect of inhibition of tumour angiogenesis inhibition is the reactivation of the host tumour immune response as the non-angiogenic endothelium is more readily stimulated to increase its adhesiveness for lymphocytes, increasing lymphocyte tumour infiltration.

2-methoxyestradiol is an anti-angiogenic, anti-proliferative cytotoxic and anti-inflammatory estradiol metabolite. The formation of catecholestrogens has been regarded as an etiological factor in the association between estradiol levels and breast cancer. The 4-hydroxy-estradiol metabolite is carcinogenic. However, epidemiological evidence suggests that there may be an inverse relationship between 2-Methoxyestradiol forming capacity (catechol-O-methyl transferase) and risk of breast cancer. In addition, 2-hydroxyestradiol does not appear to be carcinogenic and is effectively converted into 2-methoxyestradiol. 2-Methoxyestradiol has anti-proliferative effects in a variety of cell types including endothelial cells, fibroblasts, smooth muscle, granulosa cells, Chinese hamster cell lines and T lymphocytes. In addition, 2-Methoxyestradiol decreases tumour growth and shows activity in a model of arthritis provoked by intra-articular type II collagen injection. 2-Methoxyestradiol has been suggested to be of value in both atherosclerosis and rheumatoid arthritis, each of which is associated with abnormal cell division and angiogenesis.

2-methoxyestradiol is otherwise known as 1,3,5(10)-estratriene-3,17βdiol 2 methyl ether and has the following chemical formula:

2-METHYOXYESTRADIOL

It is produced in a two-step process, involving hydroxylation of estrogen to produce a catecholoestrogen followed by methoxylation to produce the corresponding methoxyoestrogen by an inducible cytochrome p450 pathway. The plasma concentrations of 2-methoxyestradiol are not well characterised, in molar levels of approximately 60 pM are detected and in pregnant females levels increase to 30 nM. Amounts in urine suggest that 2-methoxyestradiol is present in considerably lower amounts than the corresponding 2-methoxyestrone which reaches concentrations as high as 10 ng/ml of plasma during pregnancy.

D'Amato (WO 95/04535) discloses use of 2-methoxyestradiol and certain analogues in the treatment of angiogenesis related diseases. Stewart (PCT/AU97/00286) discloses 2-methoxyestradiol and analogues in the treatment of diseases characterised by airway inflammation. However, significant practical limitations are encountered with 2-methoxyestradiol: it has dose-limiting toxicity within the therapeutic range. It is highly insoluble in aqueous solution and therefore difficult to administer.

It is an object of the present invention to overcome, or at least alleviate, one or more of the difficulties or deficiencies associated with the prior art.

In one aspect, the present invention provides a conjugated prodrug of an estradiol compound, preferably of 2-methoxyestradiol or a functionally active analogue or derivative thereof, conjugated to a biological activity modifiying agent.

Preferably, the biological activity modifying agent also functions as a masking and/or targetting agent.

The biological activity modifying agent is preferably a carbohydrate or peptide moiety.

By "functionally active" is meant that the analogue or derivative of 2-methoxyestradiol has one or more of the biological activities of 2-methoxyestradiol. The biological activities of 2-methoxyestradiol include, but are not limited to: inhibition of endothelial cell proliferation; inhibition of smooth muscle cell proliferation; inhibition of tumour cell proliferation inhibition of microtubule function; inhibition of leukocyte activation. Examples of such functionally active analogues or derivatives include 2-ethoxyestradiol, 2-hydroxyestradiol and other analogues modified at the 2 position, 2methoxyestradiol-3methylether, 4-methoxyestradiol, and other analogues in which the B ring is expanded to a 7-numbered ring. See also WO95/04535, the entire disclosure of which is incorporated herein by reference.

Preferably the conjugated prodrug includes 2-methoxyestradiol or a functionally active analogue or derivative thereof, conjugated to a sugar moiety. Preferably the sugar moiety is a substrate for an enzyme which is likely to be present, or present in increased levels, in the condition to be treated. In this way, the compound will have a servocontrolled bioavailability, in that the level of enzyme is a determinant of the rate at which the drug (an estradiol compound such as 2-methoxyestradiol or functionally active analogue or derivative thereof), is released from the prodrug. This also enables localised release of the drug, for example at the site of a solid tumour.

More preferably the sugar moiety is a 5- or 6-membered sugar. A particularly preferred sugar moiety is a glucuronide, which is a substrate for glucuronidase, a tumour associated enzyme, also likely to be present in inflammatory responses. Another particularly preferred sugar moiety is a galactoside, which is a substrate for the enzyme galactosidase. Neoplastic and inflammatory diseases are associated with elevated expression of β-galactosidase and other lysosomal hydrolytic enzymes. These may convert pro-drugs to active agents at a rate which is proportional to the extent and activity of disease. This novel drug targeting mechanism results in lessening of systemic toxicity. The use of a glucuronide or galactoside conjugate of the estradiol compound such as 2-methoxyestradiol or its analogues also renders the compound water soluble and therefore increases the ease of formulation for any of the desired routes of administration.

Alternatively, the conjugated prodrug according to the present invention includes 2-methoxyestradiol or a functionally active analogue or derivative thereof, conjugated to a peptide moiety.

More preferably this peptide moiety is a tri-, tetra- or higher peptide. For example, this peptide may be, or include the sequence -Ala-Phe-Lys or -Val-L u-Lys.

The incorporation of an estradiol compound such as 2-methoxyestradiol into a disease-dependently activated pro-drug enables significant improvement of potency and selectivity of this anti-cancer and anti-inflammatory agent. Two features of disease activity are exploited by a prodrug bearing, for example, a galactoside group linked directly or via a linker to the parent molecule. β-galactosidase is upregulated in senescent endothelial cells and in macrophages that have differentiated from monocytes. Endothelial senescence is expected in areas of active angiogenesis (local endothelial cells having undergone many population doublings) and where there is significant macrophage infiltration. Both of these conditions are met in chronic inflammation in rheumatoid arthritis and in development of solid tumours. Endothelial cells proliferating to neovascularise tumours will show higher proportions of senescent cells that will express increased senescence-associated β-galactosidase. This expression, in addition to that resulting from release of leukocyte lysosomal hydrolases, serves to localise the conversion of 2-methoxyestradiol-17β-galactopyranoside. Macrophages are known to acquire increased expression of lysosomal β-galactosidase upon further differentiation induced by cytokines and phagocytic stimuli. Thus, macrophage-dependent activation of the pro-drug may also occur. 2-Methoxyestradiol itself induces an increase in expression of β-galactosidase in endothelial cells, and thus incubation of 2-methoxy-3,17β-estradiol-beta-D-galactopyranosides with endothelial cells produces a positive feedback in activation of pro-drug.

The sugar protein or peptide moiety may be conjugated to the estradiol compound at any suitable position. Preferably, the sugar, protein or peptide moiety is conjugated to the estradiol compound such as 2-methoxyestradiol or its analogues at positions 3 and/or 17.

In a particularly preferred form of this aspect of the invention, the conjugated prodrug is 17β galactopyranoside-2-methoxyestradiol or a functionally active analogue or derivative thereof. A galactoside conjugate of 2-methoxyestradiol has been found to have improved aqueous solubility and less cytotoxicity than the parent, 2-methoxyestradiol.

The sugar may be conjugated directly to the estradiol compound such as 2-methoxyestradiol or its analogue, or the two may be conjugated via a cleavable link. The cleavable link may be of any suitable type, for example a carbonate or carbamate. A suitable link may be readily determined by those skilled in the art. Use of a link may have the advantage of stabilizing the prodrug in the plasma, for example.

In a further aspect of the present invention, there is provided a compound having the formula I wherein m, n, p and q are each integers of 0, 1, 2 or 3, each $R^1$, $R^2$, $R^3$ and $R^4$ is a substituent independently selected from one or more of hydrogen, hydroxy, halo, optionally substituted $C_{1-6}$ alkyl, $C_{1-6}$ alkenyl, $C_{1-6}$ alkynyl, $C_{3-8}$ cycloalkyl, $C_{1-6}$ alkanoyl, $C_{1-6}$ alkoxy, aryl, amino, acyl, $C_{1-6}$ acyloxy aminoalkyl, imino, $C_{1-6}$ iminoalkyl, $C_1$–$C_3$ imino cycloalkyl, keto, aldehyde, hydrazono, oximino, hydroximino, $C_{1-6}$ alkoximino, $C_{3-8}$ cycloalkoximino or carboxyl groups, or an O-Protecting group, or a carbohydrate, peptide or protein residue, or derivative thereof or a pharmaceutically acceptable salt or in vivo hydrolysable ester, amide carbonate, or carbamate thereof:

with the proviso that at least one of $R^1$ to $R^4$ is present.

The compounds described above are compounds which may function as conjugated prodrugs, as described herein and/or may function as intermediates in the preparation of such conjugated prodrugs.

Any substituent may be optionally substituted, by one or more substituents, which may be the same or different. Typical substituents include: hydroxy; $C_{1-6}$alkoxy for example methoxy; mercapto; $C_{1-6}$alkylthio for example methylthio; amino; $C_{1-6}$alkylamino, for example methylamino; di-($C_{1-6}$alkyl)amino, for example dimethylamino; carboxy; carbamoyl; $C_{1-6}$alkylcarbamoyl, for example methylcarbamoyl; di-$C_{1-6}$alkylcarbamoyl for example dimethylcarbamoyl; $C_{1-6}$alkylsulphonyl, for example methylsulphonyl; arylsulphonyl, for example phenylsulphonyl; $C_{1-6}$alkylaminosulphonyl, for example methylaminosulphonyl; di-($C_{1-6}$alkyl)aminosulphonyl, for example dimethylamino-sulphonyl; nitro; cyano; cyano-$C_{1-6}$alkyl, for example cyanomethyl; hydroxy$C_{1-6}$alkyl, for example hydroxymethyl; amino-$C_{1-6}$alkyl, for example aminoethyl; $C_{1-6}$alkanoyl-amino, for example acetamido; $C_{1-6}$alkoxycarbonylamino, for example methoxycarbonylamino; $C_{1-6}$alkanoyl, for example acetyl; $C_{1-6}$alkanoyloxy, for example acetoxy; $C_{1-6}$alkyl, for example methyl, ethyl, isopropyl or tert-butyl; halo, for example fluoro, chloro or bromo; trifluoromethyl or trifluoromethoxy.

Preferably each of $R^1$ to $R^4$ is selected from hydrogen hydroxy, halo, optionally substituted $C_{1-6}$ alkyl, $C_{1-6}$ alkoxy, imino, $C_{1-6}$ iminoalkyl, $C_{3-8}$ iminocycloalkyl, keto, aldehyde, hydroximino alkoximino, hydrazono, carbamate, an O-Protecting group, or a sugar protein or peptide residue.

More preferably each of $R^1$ to $R^4$ is selected from hydroxy, $C_{1-6}$ alkoxy, imino $C_{3-8}$ iminocycloalkyl, keto, hydrazono, carbamate, or a sugar, protein, or peptide residue.

Most preferably at least one of $R^1$ to $R^4$ is a carbohydrate, peptide or protein residue or derivative thereof, or a keto, hydrazono or carbamate group.

Particularly preferred compounds according to the present invention include compounds wherein $R^1$ is one or more of hydroxy, alkoxy, acyloxy or a carbohydrate, peptide or protein residue;

$R^3$ includes an alkyl group; and $R^4$ is one or more of hydroxy, alkoxy, O-Protecting groups or a carbohydrate, protein or peptide residue.

More preferred are compounds wherein $R^1$ includes a methoxy group.

In a particularly preferred embodiment, $R^3$ includes one or more of H, a keto, a hydrazono or a carbamate group.

Compounds which may be used as conjugated prodrugs include compounds in which one of $R^1$, $R^2$, $R^3$ or $R^4$ is a sugar residue having the formula II:

II wherein Z is a spacer or bond;
m is 0 or 1; and
each of $R^5$ to $R^{12}$ are independently selected from H, OH, amino, halo, $COOR^{13}$, $CH_2OR^{13}$, $CHOH-COOR^{13}$, $PO_3H_2$, $CH_2-PO_3H_2$, $CHOH-PO_3H_2$, $CH_2COOR^{13}$, or $OCOR^{13}$;
wherein $R^{13}$ is H or an optionally substituted $C_1$ to $C_{20}$ alkyl.

Preferably, the sugar residue has the formula:

wherein $R^{14}$ is —$CH_2OH$ or —COOH.

Other compounds which may be used as conjugated prodrugs include compounds in which one of $R^1$, $R^2$ or $R^4$ is a peptide residue having the formula III:

—Z—$(ABC)_m(DF)_n(GHJK)_p$    III wherein Z is a spacer or bond
m, n and p are each integers of 0, 1 or 2
ABCDFGHJK, which may be the same or different, are each amino acids,

Where the biological activity modifying agent is a peptide moiety, the conjugated prodrug may be synthesised utilising techniques similar to those described in Franciscus et al (Franciscus et al, 2000), the entire disclosure of which is incorporated herein by reference.

Specific examples of preferred compounds according to the present invention include:
3-Acetyl 2-methoxyestradiol
3-Acetyl 6-oxo-2-methoxyestradiol
3,17-Diacetyl-2-methoxyestradiol
17-Acetyl-2-methoxyestradiol
3,17-Diacetyl-6-oxo-2-methoxyestradiol
3,17-Diacteyl-2-methoxyestradiol-6-hydrazone
2-Methoxyestradiol-6-hydrazone
2-Methoxy estradiol-17β-monodienyl ether
2-Methoxy estradiol-17β-acetate
2-Methoxy-17β-Estradiol-17-D-triacetylglucopyranosiduronic acid methyl ester
2-Methoxy-17β-Estradiol-17-D-glucopyranosiduronic acid
2,3,17β-estradiol-17-β-D-galactopyranoside-2-methyl ether
2,3,17β-estradiol-3-β-D-galactopyranoside-2-methyl ether.

Suitable pharmaceutically acceptable salts include acid addition salts such as hydrochloride, hydrobromide, citrate tartrate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine.

In vivo hydrolysable esters, amides, carbonates and carbamates hydrolyse in the human body to produce the parent compound. Such esters, amides, carbonates and carbamates can be identified by administering, for example intravenously to a test animal, the compound under test and subsequently examining the test animal's body fluids. Suitable in vivo hydrolysable groups include N-carbomethoxy and N-acetyl.

Accordingly, in a further aspect of the present invention, there is provided a conjugated prodrug of the formula:

wherein m, n, p and q are each integers of 0, 1, 2 or 3,
each $R^1$, $R^2$, $R^3$ and $R^4$ is a substituent independently selected from one or more of hydrogen, hydroxyl, halo, optionally substituted $C_{1-6}$ alkyl, $C_{1-6}$ alkenyl, $C_{1-6}$ alkynyl, $C_{3-8}$ cycloalkyl, $C_{1-6}$ alkanoyl, $C_{1-6}$ alkoxy, aryl, amino, acyl, $C_{1-6}$ acyloxy, aminoalkyl, imino, $C_{1-6}$ iminoalkyl, $C_1$–$C_3$ imino cycloalkyl, keto, aldehyde, hydrazono, oximino, hydroximino, $C_{1-6}$ alkoximino, $C_{3-8}$ cycloalkoximino or carboxyl groups, or an O-Protecting group, or a carbohydrate, peptide or protein residue, or derivative thereof, or a pharmaceutically acceptable salt or in vivo hydrolysable ester, amide, carbonate, or carbamate thereof:
with the proviso that at least one of $R^1$ to $R^4$ is present and includes a carbohydrate, protein or peptide residue.

Preferably the sugar residue is a glucuronide or galactoside, as described above. Preferably the peptide residue is, or includes the sequence D-Ala-Phe-Lys or D-Val-Leu-Lys.

In a still further aspect of the present invention there is provided a method of prophylaxis or treatment of a condition associated with angiogenesis or accelerated or increased amounts of cell division, hypertrophic growth or inflammation, said method including administering to a patient in need of such prophylaxis or treatment an effective amount of a conjugated prodrug according to the present invention, as described above.

It should be understood that prophylaxis or treatment of said condition includes amelioration of said condition.

By "an effective amount" is meant a therapeutically or prophylactically effective amount. Such amounts can be readily determined by an appropriately skilled person, taking into account the condition to be treated, the route of administration and other relevant factors. Such a person will readily be able to determine a suitable dose, mode and frequency of administration.

The pharmaceutical compositions of this invention will normally be administered to humans so that, for example, a daily dose of 0.05 to 300, preferably 150, more preferably 75 mg/kg body weight (and preferably of 0.1 to 30 mg/kg body weight) is received. This daily dose may be given in divided doses as necessary, the precise amount of the compound received and the route of administration depending on the weight, age and sex of the patient being treated and on the particular disease condition being treated accordingly to principles known in the art.

Typically unit dosage forms will contain about 1 mg to 500 mg of a compound of the present invention.

The method of the present invention may be used to prevent, ameliorate or treat inflammatory conditions, particularly conditions characterised by chronic or acute airway inflammation, such as asthma or chronic inflammatory conditions, such as rheumatoid arthritis. The method of the present invention may also be used to treat any conditions associated with enhanced angiogenesis or accelerated cell division, particularly cancers, such as solid tumours.

The patient to be treated is preferably a human, although the method of the present invention may also be used to treat other mammals such as cats, dogs, horses, sheep, pigs and cattle.

In a further aspect of the present invention there is provided a pharmaceutical composition comprising a conjugated prodrug according to the present invention, together with a pharmaceutically acceptable carrier, diluent or excipient.

The pharmaceutical composition may be used for the prophylaxis or treatment of conditions associated with angiogenesis or accelerated cell division or inflammation.

The pharmaceutical compositions including the prodrug of the present invention may be administered in standard manner for the disease condition that it is desired to treat, for example by oral, topical, parenteral (eg. intravenous, subcutaneous or intramuscular), buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions. A preferred route of administration is intravenously in sterile isotonic solution.

In the treatment of inflammatory airway conditions such as asthma, the prodrug may be administered by routes including but not limited to topical, oral, nasal and inhalation.

In addition to the compounds of the present invention, the pharmaceutical composition of this invention may also contain, or be co-administered (simultaneously or sequentially) with, one or more pharmacological agents of value in treating one or more disease conditions referred to hereinabove.

In addition, the prodrug may be incorporated into biodegradable polymers allowing for sustained release, the polymers being implanted in the vicinity of where delivery is desired, for example, at the site of a tumour. The biodegradable polymers and their use are described in detail in Brem et al., *J. Neurosurg.*, 74:441–446 (1991).

A person skilled in the art will be able by reference to standard texts, such as Remington's Pharmaceutical Sciences 17th edition, to determine how the formulations are to be made and how these may be administered.

Such formulation techniques include the step of bringing into association the prodrug and the pharmaceutically acceptable carrier(s), diluent(s) or excipient(s). In general, the formulations are prepared uniformly and intimately bringing into association the prodrug with liquid carriers or finely divided solid carriers or both, and then, if necessary, shaping the product.

In a further aspect of the present invention there is provided use of a conjugated prodrug according to the present invention for the preparation of a medicament for the prophylaxis or treatment of conditions associated with angiogenesis or accelerated cell division or inflammation.

In a still further aspect of the present invention there is provided a method of preparing a compound of formula I as described above which method includes:

(a) reacting a compound of formula IV, V or VI with a compound of formula VII or VII:

-continued

VII

L—Z—(ABC)$_m$(DF)$_n$(GHJK)$_p$   VIII wherein R$^1$, R$^2$, R$^3$, R$^4$, ABCDFGHJK and m, n, p and q are as defined in claims 10 and 18 except that in formula IV,
q is 0, 1 or 2;
in Formula V, m is 0, 1 or 2 and
in Formula VI, n is 0, 1 or 2
R$^5$ to R$^{12}$ are as defined above,
L is a leaving group,
Z is a spacer or bond;
wherein any functional group is protected, if necessary; and (b) removing any protecting groups;
(c) optionally, before or after said reaction converting any compound of formula III, V or VI into another compound of formula IV, V or VI;
(d) optionally forming a pharmaceutically acceptable salt or in vivo hydrolysable ester, amide, carbonate or carbamate.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

A carboxyl protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C) alkyl groups (eg. isopropyl, t-butyl); lower alkoxy lower alkyl groups (eg. methoxymethyl, ethoxymethyl, isobutoxymethyl); lower aliphatic acyloxy lower alkyl groups, (eg. acetoxymethyl, propionyloxymethyl, butryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg. benzyl, p-methoxybenzyl, o-nitrobenzyl, p-nitrobenzyl, benzhydryl and phthalidyl); tri(lower alkyl)silyl groups (eg. trimethylsilyl and t-butyldimethylsilyl); tri(lower alkyl)silyl lower alkyl groups (eg. trimethylsilylethyl); and (2–6C) alkenyl groups (eg. allyl and vinylethyl).

Methods particularly appropriate for the removal of carboxyl protecting groups include for example acid, base-, metal- or enzymically-catalysed hydrolysis.

Examples of hydroxyl protecting groups include lower alkyl groups (eg. t-butyl), lower alkenyl groups (eg. allyl); lower alkanoyl groups (eg. acetyl); lower alkoxycarbonyl groups (eg. t-butoxycarbonyl); lower alkenyloxycarbonyl groups (eg. allyloxycarbonyl); aryl lower alkoxycarbonyl groups (eg. benzoyloxycarbonyl, p-methoxybenzyloxycarbonyl, o-nitrobenzyloxycarbonyl, p-nitrobenzyloxycarbonyl); tri(lower alkyl)silyl (eg. trimethylsilyl, t-butyldimethylsilyl) and aryl lower alkyl (eg. benzyl) groups. An acetyl group is preferred.

Examples of amino protecting groups include formyl, aralkyl groups (eg. benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (eg. t-butoxycarbonyl); lower alkenyloxycarbonyl (eg. allyloxycarbonyl); aryl lower alkoxycarbonyl groups (eg. benzyloxycarbonyl, p-methoxybenzyloxycarbonyl, o-nitrobenzyloxycarbonyl, p-nitrobenzyloxycarbonyl); trialkylsilyl (eg. trimethylsilyl and t-butyldimethylsilyl); alkylidene (eg. methylidene); benzylidene and substituted benzylidene groups.

Methods appropriate for removal of hydroxy and amino protecting groups include, for example, acid-, base-, metal- or enzymically-catalysed hydrolysis, for groups such as 2-nitrobenzyloxycarbonyl, hydrogenation and for groups such as o-nitrobenzyloxycarbonyl, photolytically.

Pharmaceutically acceptable salts of the compound of the formula (I) may be prepared in any conventional manner for example from the free base and acid. In vivo hydrolysable esters, amides and carbamates may be prepared in any conventional manner.

The reaction between the compounds of the formulae IV, V or VI and VII or VIII is performed in conventional manner. Typically this reaction takes place in organic solvent for example an anhydrous aprotic solvent such as dimethylformamide, dimethylacetamide, tetrahydrofuran, toluene or benzene. The reaction is generally performed in the presence of a catalyst, such as a cadmium salt for example cadmium carbonate, and is generally performed at ambient or elevated temperature for example 0°–100° C., more preferably 40°–80° C.

In the compounds of the formula IV, V, VI, VII or VIII, L is a conventional leaving group such as a hydrogen ion, halo for example chloro, iodo or bromo; or a tosylate for example p-toluenesulphonyloxy or methanesulphonyloxy.

The compound of formula VII may be a protected sugar derivative, preferably an acetylated sugar. The acetylated sugar may be of any suitable type. Preferably the acetylated sugar is an acetyl glucuronate or acetyl galactoside.

Compounds of the formula IV, V, VI, VII or VIII which has a protecting group may be deprotected in standard manner. Any suitable N-protecting group may be used and deprotected in conventional manner. Favourably the protecting group is $C_{1-6}$alkoxycarbonyl and such compounds may be converted to compounds of the formula (I) wherein R is methyl for example by treating with a reducing agent such as lithium aluminium hydride. Certain compounds of the formula (V) are also in vivo hydrolysable esters, amides, carbonates or carbamates of the compounds of the formula (I).

Compounds of the formula IV, V or VI wherein R$^1$ to R$^4$ is hydrogen may be converted to compounds wherein R$^1$ to R$^4$ is other than hydrogen. For example such conversion may comprise conventional methods of alkylation with an appropriate alkylating agent or reductive amination. For example an isopropyl group may be prepared by reacting a compound wherein R is hydrogen with acetone in the presence of a reducing agent such as sodium borohydride or sodium cyanoborohydride. A 2-methylpropyl group may be prepared by reacting a compound wherein R is hydrogen with isobutyric acid in the presence of a reducing agent such as sodium borohydride or sodium cyanoborohydride.

Preferably the reaction is conducted in the presence of a catalyst. The catalyst may be of any suitable type. Preferably the catalyst is a cadmium salt such as cadmium carbonate.

The product may be isolated by any suitable technique(s) as will be readily apparent to an appropriately skilled person. Filtration, flash chromatography and preparative HPLC have been found to be suitable.

The present invention will now be more fully described with reference to the accompanying Examples. It should be understood, however, that the description following is illustrative only and should not be taken in any way as a restriction on the generality of the invention described above.

EXAMPLE 1

Figure 1:
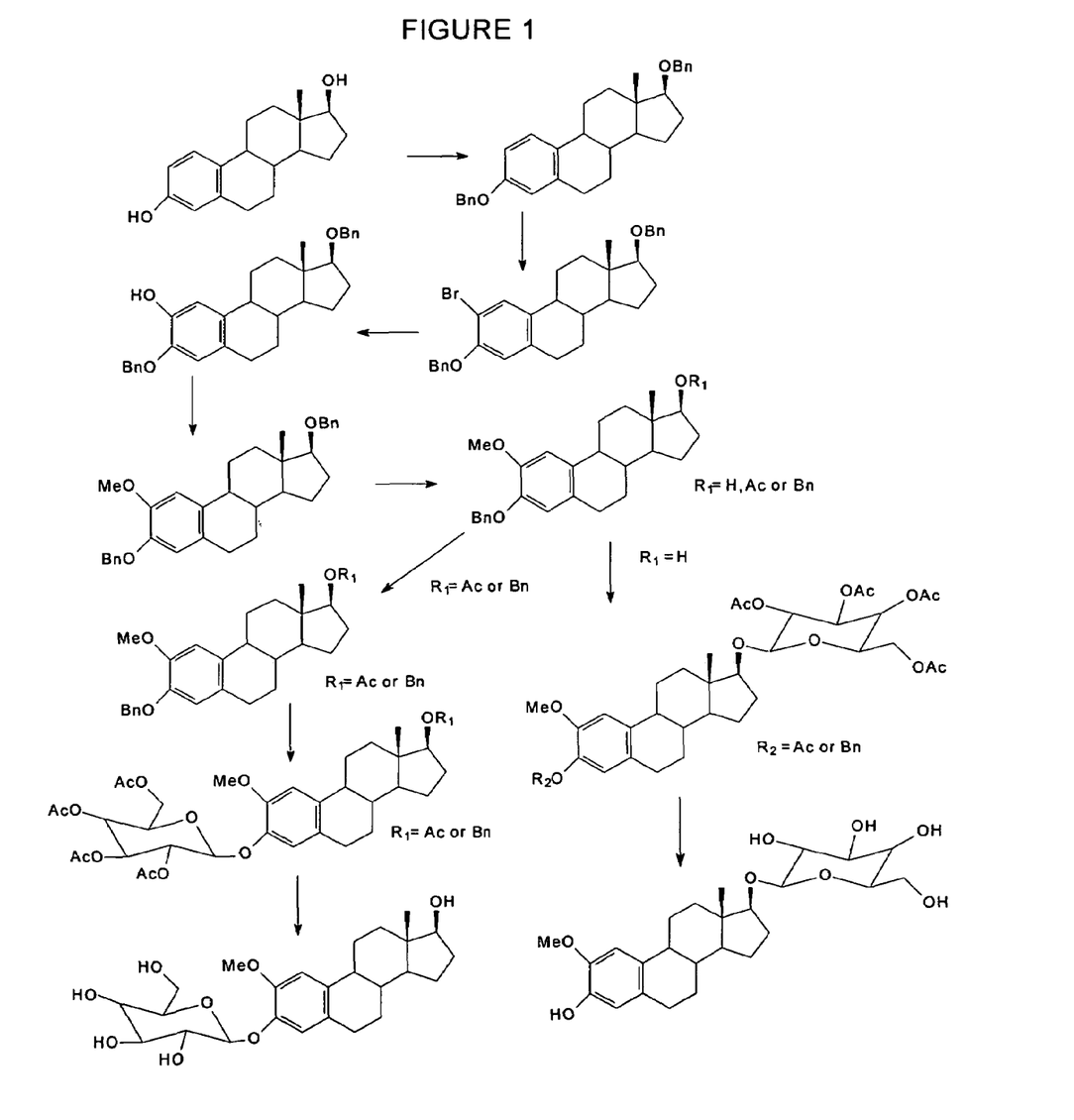

Synthesis of 2-Methoxy-17β-Estradiol-17-D-glucopyranosiduronic acid (See FIG. 1)

β-Estradiol Dibenzyl Ether (2)

β-Estradiol (20.00 g, 73.4 mmol) was dissolved in 300 mL anhydrous DMF and cooled to 0° C. under nitrogen. Sodium Hydride (10.4 g, 260 mmol) was added in portions with constant stirring. Stirring continued at 0° C. for a further 15 minutes at which time Benzyl Bromide (40.0 mL, 336 mmol) was added dropwise followed by addition of tetrabutylammoniumiodide (2.0 g, 5.4 mmol). Stirring of reaction then continued at room temperature for 72 hours. The reaction mixture was cooled to 0° C. and excess Sodium hydride quenched with 100 mL 50% aqueous Ethanol. The reaction mixture was acidified to pH 3 with 3M HCl solution. Total reaction mixture was then evaporated in vacuo to a volume of approximately 300 mL and extraction was performed with 3×150 mL Ethyl Acetate in the presence of saturated Sodium Chloride solution (200 mL). Combined extracts were washed with water (200 mL), saturated Sodium Chloride solution (200 mL), and dried over anhydrous Sodium Sulphate and evaporated in vacou to give a viscous orange oil. Trituration with Petroleum Spirit yielded a cream coloured solid (26.3 g 76.8% yield). TLC analysis of the product indicated a single spot.

2-Bromo-β-Estradiol Dibenzyl Ether (3)

A stirred solution of β-Estradiol Dibenzyl Ether (18.60 g, 41.1 mmol) in 120 mL anhydrous THF/180 mL Acetic Acid was cooled below −10° C. under nitrogen. Bromine (2.53 mL, 49.4 mmol) was added dropwise over a 30 minute period ensuring temperature remained at or below −10° C. Stirring continued at −10° C. for 30 minutes before reaction was warmed to room temperature and stirring continued for a further 2.5 hours. Reaction mixture was poured onto an ice/water mixture (400 mL) and extraction performed with 3×200 mL of Dichloromethane with combined organic layers being washed with water (200 mL), saturated Sodium Bicarbonate solution (200 mL), 10% Sodium Thiosulphate solution (200 mL) and water (200 mL) and dried over anhydrous Sodium Sulphate. Evaporation yielded a gluggy cream solid which was recrystallised from Ethyl Acetate to give a cream coloured crystalline solid (13.21 g, 60.5%). TLC analysis indicated a single spot.

2-Hydroxy-β-Estradiol Dibenzyl Ether (4)

A stirred solution of 2-Bromo-β-Estradiol Dibenzyl Ether (10.00 g, 18.8 mmol) in 200 mL anhydrous THF was cooled to −78° C. under nitrogen and a 1.7M solution of t-butyl-ithium in Pentane (24.35 mL, 41.4 mmol) was added dropwise ensuring reaction temperature remained below −70° C. Reaction mixture was stirred at this temperature for 15 minutes at which time MoOPH reagent (9.08 g, 20.7 mmol) was added dropwise as a suspension in anhydrous THF ensuring reaction temperature remained below −70° C., with stirring continuing at this temperature for a further 1 hour, before reaction was warmed to 0° C. and stirred for a further 1 hour. Reaction mixture was quenched dropwise addition of water followed by extraction with 3× 150 mL Dichloromethane. Combined organic layers were washed with 50% water/50% saturated Sodium Chloride solution (150 mL), Saturated Sodium Bicarbonate solution (150 mL) and saturated Sodium Chloride solution (150 mL) prior to being dried over anhydrous Sodium Sulphate. Evaporation yielded the crude product as a dark green viscous oil. TLC analysis showed an impure product that was purified by flash chromatography to yield 5.56 g (63.2%) of the pure product.

2-Methoxy-β-Estradiol Dibenzyl Ether (5)

Anhydrous Potassium Carbonate (12.03 g, 87.0 mmol) was added to a stirred solution of 2-Hydroxy-β-Estradiol Dibenzyl Ether (4.08 g, 8.7 mmol) in anhydrous DMF (250 mL) under nitrogen. Reaction mixture was stirred at room temperature for 15 minutes prior to dropwise addition of Iodomethane (8.13 mL, 130.5 mmol), followed by addition of tetrabutylammoniumiodide (0.48 g, 1.3 mmol) as phase transfer catalyst. Stirring continued at room temperature for a further 90 hours at which time extraction was performed with Ethyl Acetate (3×200 mL) in the presence of 50% water/50% saturated Sodium Chloride solution (300 mL). Combined extracts were washed with water (200 mL), 1M Sodium Hydroxide solution (2×200 mL) and saturated Sodium Chloride solution (200 mL) before drying over anhydrous Sodium Sulphate. Evaporation yielded a pale yellow oil (3.93 g, 94.3%) that solidified on standing. TLC analysis indicated only a single component to be present.

2-Methoxy-β-Estradiol (6)

2-Methoxy-β-Estradiol Dibenzyl ether (1.41 g, 2.9 mmol) was dissolved in Ethyl Acetate (30 mL) and acidified with 1 M HCL in Diethyl Ether (3 mL). 10% Palladium on Carbon (777 mg, 0.73 mmol) was added and reaction put on Parr hydrogenator at an initial hydrogen pressure of 65 psi for 48 hours. Catalyst was removed by filtration through a celite pad which was washed with Dichloromethane (3×30 mL). Evaporation of filtrate gav a pale yellow oil that solidified on standing. TLC analysis indicated two products which were separated by flash chromatography (Ethyl Acetate:Petroleum Spirit 3:7 v/v and 1:1 v/v) to yield the product (6) as a cream coloured solid (560 mg, 63.8%) and acetate byproduct (7) (230 mg, 22.9%) as a white solid.

Further quantities of (6) were obtained from hydrolysis of 2-Methoxy-17β-Acetyloxy-Estradiol (7) (1.39 g, 4.0 mmol) which was dissolved in THF (25 mL) and stirred under nitrogen. An aqueous solution of 0.4M Lithium Hydroxide (22.2 mL, 8.9 mmol) was added dropwise and stirring continued for 23 hours at room temperature. A small amount of acetate product was present at this time by TLC, with further Lithium Hydroxide (5.0 mL, 2.0 mmol) solution being added. Reaction mixture continued stirring for a further 1 hour at room temperature prior to acidification to pH 3 with 1M HCl solution. Extraction was performed with 3×25 mL Dichloromethane with combined extracts being washed with water (25 mL) and saturated Sodium Chloride solution (25 mL). Drying over anhydrous Sodium Sulphate and evaporation yielded a yellow crystalline solid (1.20 g, 98.3%). The product was separated by flash chromatography (Ethyl Acetate:Petroleum Spirit 3:7 v/v and 1:1 v/v) to yield the product (6) as a cream coloured solid (921 mg, 75.5%) and acetate starting material (7) (110 mg, 7.9%) as a white solid.

2-Methoxy-17β-Estradiol-17-D-triacetylglucopyranosiduronic acid methyl ester (8)

A mechanically stirred solution of 2-Methoxy-β-Estradiol (500 mg, 1.65 mmol) in toluene (25 mL) and Cadmium Carbonate (177 mg, 4.95 mmol) was refluxed to approximately half volume via a dean stark apparatus ensuring complete dryness of reaction. To this was added dropwise a solution of 1α-Bromo-2,3,4-tri-O-acetylglucuronate (397 mg, 4.95 mmol) in anhydrous toluene (25 mL) and collection via the dean stark trap continued until volume of reaction mixture was approximately 25 mL. Reflux continued for a total of five hours at which time the catalyst was removed by filtration through a celite pad which was thoroughly washed with toluene. Evaporation yielded 1.06 g of a buff coloured foam which was purified initially by flash chromatography then preparative HPLC to give 282 mg (27.6%) of product.

2-Methoxy-17β-Estradiol-17-D-glucopyranosiduronic acid (9)

To a stirred solution of 9 (245 mg, 0.40 mmol) in absolute Ethanol 15 mL was added 5M Sodium Hydroxide solution (0.5 mL). Reaction was stirred at room temperature for 1.5 hours prior to the pH being adjusted to ~3 with 0.2M Sulphuric Acid. Upon evaporation a small sample of the crude mixture (~12 mg) was purified by preparative HPLC to yield 7 mg of a white washed solid crystalline product (9).

EXAMPLE 2

Synthesis of 2-methoxy-3,17β-estradiol-β-D-galactopyranosides 3,17β-Estradiol is initially bis protected as the 3-17β-dibenzyl ether by deprotonation with sodium hydride and subsequent reaction with benzyl bromide in DMF in the presence of tetrabutylammonium iodide. After workup the bis-protected product is obtained in high yield without the need for lengthy purification. 3-17β-Estradiol dibenzyl ether is brominated at the 2-position, in a THF/acetic acid mixture, with a high degree of regioselectivity (>80%). Recrystallization from ethyl acetate gives pure 2-bromo-3,17β-estradiol dibenzyl ether in good yield, followed by halogen-lithium exchange at low temperature with t-butyllithium. Reaction of the lithiated intermediate with MoOPH reagent (a molybdenum pentoxide complex) and subsequent reductive workup yields 2-hydroxy-3,17β-estradiol dibenzyl ether in good yield. Chromatographic purification is required at this point, but is relatively simple given the product impurity profile.

Quantitative methylation is effected by deprotonation of the phenol with potassium carbonate and subsequent alkylation with iodomethane in DMF. Hydrogenolysis of the 2-methoxy dibenzyl protected steroid may be performed under positive hydrogen pressure in the presence of 10% palladium on carbon. The product, 2-methoxy 3-17β-estradiol, is obtained as a white or pale yellow solid. This procedure incorporates a similar synthetic process to that of Cushman et al, 1997, but with improved yields and a more direct and reliable 2-hydroxylation process.

Careful selection of hydrogenolysis conditions, allows selective formation of a number of different products. The 17β-monobenzylether of 2-methoxyestradiol can be produced, as can the 17β-acetate. Depending on subsequent reaction conditions, and the degree of hydroxyl protection required, this can be most advantageous. Protection of the 3-hydroxyl function of 2-methoxyestradiol may be selectively performed by formation of the acetate under mild conditions or further benzyl protection as the 3-monobenzyl ether by standard methods.

Condensation of these compounds via a modified Königs-Knorr method, with 2,3,4,6-tetra-O-acetyl-α-galactopyranosyl bromide in the presence of cadmium carbonate, and subsequent deprotection produces the corresponding 3-(β-D) or 17-(β-D)-saccharide (Blackwell et al, 1993). The 2,3,4,6-tetra-O-acetyl-α-glucopyranosyl bromide may also be used at this reaction step to give the corresponding 3 or 17β-(β-glucopyranosyl) substituted steroids (Paulsen, 1982).

EXAMPLE 3

Figure 2:
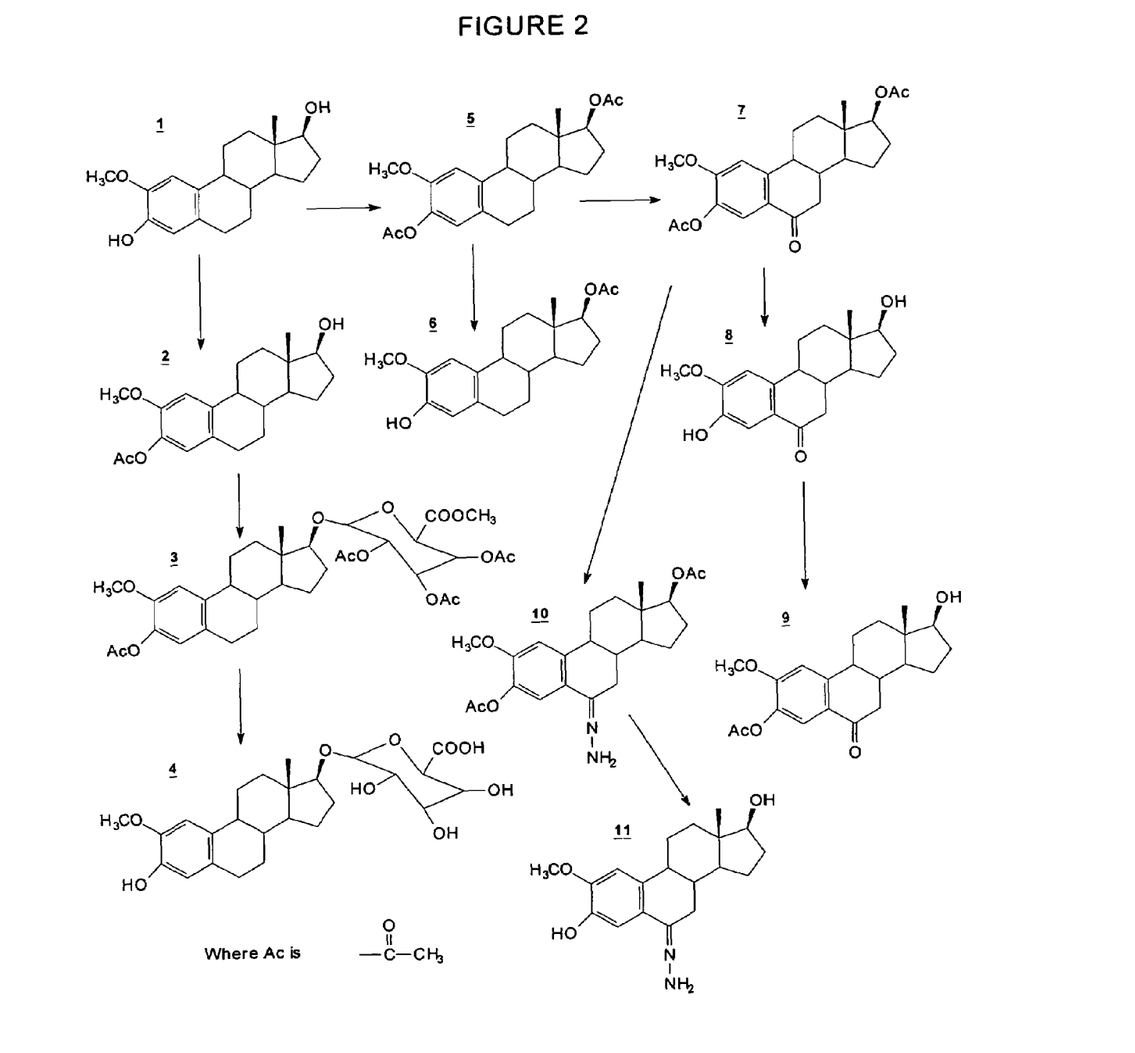

Synthesis of Various 2-methoxyestradiol (1) Analogues and Derivatives (See FIG. 2)

3-Acetyl 2-methoxyestradiol (2)

2-Methoxyestradiol (105 mg, 0.347 mmol) was dissolved in anhydrous pyridine (6.0 mL) under a nitrogen atmosphere and was cooled to −40° C. (acetonitrile/$CO_2$ bath). Acetic anhydride (3.0 mL) was added dropwise over a ten minute period and the reaction left stirring at low temperature for 165 minutes at which time 50 mL of 1M HCl was added and the reaction allowed to warm to room temperature. Extraction was performed with ethyl acetate (3×50 mL) then the combined organic extracts were sequentially washed with 3M aqueous HCl (50 mL), water (50 mL) and saturated aqueous NaCl solution (50 mL). The organic layers were dried over sodium sulphate then filtered and the solvent evaporated in vacuo to give a viscous oil. Purification was performed by flash chromatography (1:1 ethyl acetate/petroleum spirit) to yield the title compound as a white solid (87 mg, 71%).

$R_f$ 0.48 [ethyl acetate-petroleum spirit (1:1), silica gel]; $^1$H NMR ($CDCl_3$): d6.87(s, 1H), 6.71 (s, 1H), 3.78(s, 3H), 3.71 (t, J=8.5 Hz, 1H), 2.78–2.73(m, 2H), 2.28(s, 3H), 2.30–1.15 (m, 13H), 0.76(s, 3H)

Methyl 3-acetyl-2-methoxyestradiol-17-b-D-2',3',4'-tri-O-acetylglucopyranosiduronate (3)

Freshly dried cadmium carbonate (73.7 mg, 0.428 mmol) was added to a solution of 3-acetyl-2-methoxyestradiol (2) (36.8 mg, 0.107 mmol) in anhydrous toluene (40 mL) under a nitrogen atmosphere. The suspension was heated at reflux until 20 mL of solvent had collected in a Dean-Stark trap. At this time, a solution of methyl 1-bromo-1-deoxy-2,3,4-tri-O-acetyl-a-D-glucopyranuronate (127.4 mg, 0.321 mmol) in toluene (20 mL) was added dropwise at approximately the same rate as that of the continuing distillation into the Dean-Stark trap. After 60 minutes of reaction, a further quantity of methyl 1-bromo-1-deoxy-2,3,4-tri-O-acetyl-a-D-glucopyranuronate (84.9 mg, 0.214 mmol) was added in toluene (10 mL) and a further 10 mL of solvent distilled. The reaction was then held at reflux for 27 hours before cooling to room temperature. Solids were removed by filtration through a celite pad that was thoroughly washed with toluene. The combined filtrate and washings were sequentially washed with 1M aqueous HCl (30 mL), water (30 mL), and saturated aqueous NaCl (30 mL). The organic layer was dried over sodium sulphate then filtered and evaporated to dryness to yield 133 mg of a tan oil. Partial purification was performed using flash chromatography ($SiO_2$, 0.5:5:94.5 triethylamine/diethylether/dichloromethane) to give the title compound in slightly impure form (67.0 mg).

$R_f$ 0.42 [diethylether-dichloromethane (1:19), silica gel].

2-Methoxyestradiol-17-b-D-glucopyranosiduronic acid (4)

Slightly impure glucopyranosiduronate (3) (approx 67.0 mg) was dissolved in methanol (15.0 mL) and 0.5M NaOH aqueous solution (1.5 mL) was added with stirring under a nitrogen atmosphere. Stirring was continued at room temperature for 18 hours at which time the reaction mixture was diluted to approximately 75 mL with water and the pH of the reaction mixture was adjusted to pH 8.0 with 0.5M aqueous HCl. The aqueous solution was washed with diethyl ether (2×10 mL), prior to further pH adjustment to pH 2.5. The aqueous solution was washed with dichloromethane (2×10 mL) and extraction performed with t-butyl methyl ether (5×10 mL). The combined t-butyl methyl ether layers were dried over sodium sulphate then filtered and the solvent evaporated in vacuo to give the title compound as a white/cream crystalline solid (24.8 mg, 48.5% over the two step process).

mp 181–182° C. (dec); $^1$H NMR ($CD_3OD$): d6.79(s, 1H), 6.47(s, 1H), 4.41(d, J=7.6 Hz, 1H) 3.79(s, 3H), 3.75(t, J=8.4 Hz, 1H), 3.51 (t, J=9.4 Hz, 1H), 3.36(t, J=9.2 Hz, 1H), 3.31–3.29(m, 1H), 3.22(t, J=8.4 Hz, 1H), 2.78–2.62(m, 2H), 2.33–2.24(m, 1H), 2.20–1.94(m, 3H), 1.73–1.63(m, 2H), 1.50–1.16(m, 6H), 0.87(s, 3H); K[partition coefficient](1-octanol/water)=0.372.

3,17-Diacetyl-2-methoxyestradiol (5)

2-Methoxyestradiol (127.5 mg, 0.426 mmol) was dissolved in anhydrous pyridine (6.0 mL) under a nitrogen atmosphere and cooled to 0° C. Acetic anhydride (3.0 mL) was added dropwise and the reaction allowed to warm to room temperature. After overnight stirring, the reaction mixture was cooled to 0° C. at which time 50 mL of 1M aqueous HCl was added and the reaction allowed to warm to room temperature. Extraction was performed with ethyl acetate (3×50 mL) and the combined combined organic extracts were sequentially washed with 3M aqueous HCl (50 mL), water (50 mL) and saturated aqueous NaCl (50 mL). The organic layers were dried over sodium sulphate then filtered and the solvent evaporated in vacuo to give a white solid (154 mg). The product was homogeneous when analysed by TLC therefore purification was deemed unnecessary, however an analytical sample was purified on a silca gel column using 1:5 ethyl acteate/petroleum spirit as eluant.

$R_f$ 0.88[ethyl acetate-petroleum spirit (1:1), silica gel]; $^1$H NMR ($CDCl_3$): d 6.86(s, 1H), 6.71 (s, 1H), 4.67(t, J=8.3 Hz, 1H), 3.78(s, 3H), 2.77–2.74(m, 2H), 2.28(s, 3H), 2.04(s, 3H), 2.26–1.23(m, 13H), 0.81 (s, 3H)

17-Acetyl-2-methoxyestradiol (6)

Activated zinc (4×1 g portions) was added to a stirred solution of 3,17-diacetyl-2-methoxyestradiol (5) (154 mg) in methanol (25 mL) at time points of 0, 64, 94 and 118 hours. After this time, solids were removed by filtration through a celite pad that was then thoroughly washed with methanol and dichloromethane. The combined organic filtrates and washings were washed with water (10 mL) and saturated aqueous NaCl solution (10 mL) prior to drying over sodium sulphate and filtration. Evaporation of the organic solvents in vacuo yielded 103.5 mg of a white crystalline solid. (103.5 mg, 71.3% over the two step process).

$R_f$ 0.70[ethyl acetate-petroleum spirit-acetic acid (20:78: 2), silica gel]; $^1$H NMR ($CDCl_3$): d6.86(s, 1H), 6.71(s, 1H), 4.67(t, J=8.3 Hz, 1H), 3.78(s, 3H), 2.77–2.74(m, 2H), 2.04 (s, 3H), 2.26–1.23(m, 13H), 0.81 (s, 3H).

3,17-Diacetyl-6-oxo-2-methoxyestradiol (7)

Chromium trioxide (79.8 mg, 0.798 mmol) was dissolved with stirring over a 90 minute period in 2.0 mL of 90% (v/v) aqueous acetic acid. This oxidizing agent was added dropwise at 10° C. to a stirred solution of 3,17-diacetyl-2-methoxyestradiol (5) (72.5 mg, 0.188 mmol). The mixture was stirred at 10° C. for 30 minutes at which time the reaction was poured onto an ice/water mixture (30 mL) which was extracted with ethyl acetate (3×15 mL). The combined extracts were washed with water (20 mL), saturated aqueous $NaHCO_3$ (20 mL), water (20 mL), and saturated aqueous NaCl (20 mL) prior to drying over sodium sulphate and filtration. Evaporation of the organic solvent yielded a solid yellow residue. This residue was purified by flash chromatography on silica gel using a 1:3 ethyl acetate/petroleum spirit mixture as eluant to give a white solid (34 mg, 45.3%).

$R_f$ 0.36[ethyl acetate-petroleum spirit (1:3), silica gel]; $^1$H NMR ($CDCl_3$): d7.73(s, 1H), 6.92(s, 1H), 4.71(t, J=8.5 Hz, 1H), 3.90(s, 3H), 2.69(dd, J=16.9, 3.4 Hz, 1H), 2.53 (dt, J=16.9, 3.4 Hz, 1H), 2.31(s, 3H), 2.06(s, 3H), 2.40–1.34(m, 13H), 0.83(s, 3H); $^{13}$C NMR ($CDCl_3$): d195.81, 171.10, 168.92, 155.40, 146.95, 138.42, 126.06, 121.79, 108.36, 82.09, 55.97, 49.74, 43.49, 43.26, 42.63, 39.57, 36.38, 27.36, 25.35, 22.92, 21.12, 20.52, 11.84.

6-Oxo-2-methoxyestradiol (8)

Anhydrous potassium carbonate (20 mg, 0.145 mmol) was added to a stirred solution of 3,17-diacetyl-6-oxo-2-methoxyestradiol (7) (34 mg, 0.085 mmol) in 8.0 mL of methanol under a nitrogen atmosphere. Water (3.0 mL) was added and reaction stirred at room temperature for 16 hours. At this time, the pH of the reaction was adjusted to pH 4 with dropwise addition of 1M HCl aqueous solution. Extraction was performed with ethyl acetate (3×10 mL) then the combined layers were washed with water (10 mL) and saturated aqueous NaCl solution (10 mL) prior to drying over sodium sulphate and filtration. Evaporation of the solvent in vacuo yielded a cream coloured solid which was purified by flash chromatography on silica gel (3:2 ethyl acetate: petroleum spirit) to give 26.4 mg (98.3%) of the target compound as a white crystalline solid.

mp 189–190° C. (dec); $R_f$ 0.34[ethyl acetate-petroleum spirit (3:2), silica gel]; $^1$H NMR ($CD_3OD$): d7.36(s, 1H), 6.91 (s, 1H), 3.92(s, 3H), 3.66(t, J=8.5 Hz, 1H), 2.52(dd, J=16.8, 3.5 Hz, 1H), 2.43–1.26(m, 12H), 0.76(s, 3H);

3-Acetyl 6-oxo-2-methoxyestradiol (9)

6-Oxo-2-methoxyestradiol (8) was dissolved in anhydrous pyridine (4.0 mL) with stirring under a nitrogen atmosphere and the solution cooled to −40° C. (acetonitrile/$CO_2$ bath). Acetic anhydride (2.0 mL) was added dropwise over a ten minute period at this temperature, and the reaction was allowed to stir at −40° C. for 165 minutes prior to quenching with water (10 mL). Extraction was performed with ethyl acetate (3×20 mL) and the combined organic layers were washed with 3M aqueous HCl (2×20 mL), saturated aqueous NaCl (20 mL) and dried over sodium sulphate then filtered prior to evaporation of the solvent in vacuo to yield a pale yellow oil (30.2 mg). Purification of the title compound was performed by short column chromatography on silica gel (1:3 ethyl acetate/petroleum spirit) to give a white solid (14.2 mg, 47.5%).
$^1$H NMR ($C_6D_6$): d8.31(s, 1H), 6.54(s, 1H), 3.30(s, 3H), 3.37(t, J=8.6 Hz, 1H), 3.30(s, 3H), 2.60(dd, J=16.8, 3.6 Hz, 1H), 2.01–0.63(m, 12H), 0.57(s, 3H);

3,17-Diacteyl-2-methoxyestradiol-6-hydrazone (10)

Sodium acetate (144 mg, 1.755 mmol) was suspended in a solution of 3,17-diacetyl-6-oxo-2-methoxyestradiol (7) (35.5 mg, 0.089 mmol) in anhydrous methanol (25.0 mL) under a nitrogen atmosphere. Hydrazine hydrate (6 drops) was added and the reaction stirred at room temperature for 2 hours. The reaction mixture was then heated to reflux for a further 2 hours and then glacial acetic acid (10 drops) was added. After this, the reaction continued at reflux for a further 4.5 hours then glacial acetic acid (5 drops) was added. The reaction was continued at reflux for a further 1.5 hours after which time a further 8 drops of glacial acetic acid and 5 drops of hydrazine hydrate were added and reflux continued for 3 hours. Upon cooling to room temperature, the solvents were evaporated to give a bright yellow semisolid. This residue was dissolved in 20 mL of water and extraction performed with dichloromethane (3×50 mL). The combined organic layers were then washed with water (20 mL) and dried over sodium sulphate then filtered. Evaporation of the solvent in vacuo gave the target hydrazone product.
$R_f$ 0.24[ethyl acetate-petroleum spirit (1:1), silica gel]; $^1$H NMR (CDCl$_3$): d7.86(s, 1H), 6.81(s, 1H), 4.69(t, J=8.3 Hz, 1H), 3.94(s, 3H), 3.37(dd, J=17.6, 3.9 Hz, 1H), 2.06(s, 3H), 2.04(s,3H), 2.38–1.21 (m, 12H), 0.83(s, 3H); ESIMS-M+1 m/z=415.1.

2-Methoxyestradiol-6-hydrazone (11)

A small sample (ca. 5 mg) of 3,17-diacetyl-2-methoxyestradiol-6-hydrazone (10) was suspended in anhydrous methanol (75 mL) in the presence of a large excess of anhydrous potassium carbonate. The reaction mixture was stirred overnight at room temperature and the pH adjusted to pH 5 with a combination of 1M aqueous NH$_4$Cl and 2M aqueous HCl. The residual methanol was evaporated in vacuo and the aqueous residue extracted with dichloromethane (3×50 mL). The combined organic phases were washed with water and dried over sodium sulphate then filtered. Evaporation of the solvent in vacuo yielded a yellow solid that was recrystallised from chloroform.
$R_f$ 0.30[ethyl acetate-petroleum spirit (4:1), silica gel].

EXAMPLE 4

Susceptibility of 2-methoxyestradiol-17β-D-glucuronide to Metabolism by Glucuronidase 2-MEG was incubated with purified *E. Coli*-derived β-glucuronidase for 16 hours (rat renal homogenate for 5.5 hours) in Tyrodes buffer. At the end of these incubation periods, extraction was carried out by using 100 μl of reaction mixture with 200 μl of acetonitrile (ACN) followed by the addition of 5 μl 2M HCL, vortexing and centrifugation at 1500 g (ambient temperature). Samples of enzyme incubates or quality control incubates were then chilled at −20° C. for at least 10 min, prior to removal of 120 μl of the upper (ACN) phase which is added to 120 μl distilled H$_2$O. One hundred μl of this extract was injected into a Hewlett Packard Series 1050 HPLC fitted with a C18 analytical column (Hypersil ODS 3 μM, 4.6×150 mm) guarded by a pre column (Alltech Hypersil ODS 3 μM; 4.6×7.6 mm) and metabolites were detected with a Hewlett Packard 1046A fluorescence detector (I excitation 270 nm, emission, 320 nm). Metabolites were separated in a mobile phase of ACN buffer of 40:60 (buffer comprised 20 mM NaH$_2$ PO$_4$, 0.02% orthophosphoric acid, pH 3.1–3.2) at a flow rate of 0.7 ml/min. for the first 4 min with a linear gradient to a mobile phase of ACN: buffer (76:24) at 4.5 min. which was maintained for the remainder of the separation (10 min).

Quantitative recovery of quality control standards was achieved. 2-MEG eluded with a retention time of 4.35 min and 2-MEO of 9.8 min. The fluorescence of 2-MEO was approximately 5 fold that of 2-MEG (FIG. 3). It is evident that appreciable conversion of 2-MEG to 2-MEO occurs during incubation with either *E. Coli* β-glucuronidase (~20% conversion) and rat renal homogenates (~6%) during incubation periods of 16 hours and 5.5 hours, respectively.

EXAMPLE 5

Regulation of Airway Mesenchymal Cell Number and DNA Synthesis by 2-methoxyestradiol and 2-methoxyestradiol-17β-D-glucuronide Human airway fibroblasts were obtained from volunteers in a follow-up of the Melbourne Epidemiological Survey of Childhood Asthma (MESCA) (Oswald et al., 1994) initially recruited at age 7 in 1965 and now 42 years old. Volunteers underwent bronchial biopsy which provided tissue samples of epithelium and mucosa of approximately 2 mm$^3$. These specimens were dissected to remove the epithelium and placed in plastic culture plates. Fibroblasts grew by explant culture over a six week period when maintained according to previously described methods (Zhang et al., 1996). Cells were seeded at subconfluent densities onto six cell plates and after 72 hours were rendered quiescent by serum deprivation. Twenty four hours after serum removal, cells were exposed to thrombin (0.3 U/ml) together with a serum-free medium supplement containing insulin, transferrin and selenium. Cells were harvested by incubation with Trypsin (0.5% w/v) for 10 min. or until a single cell suspension was produced. Cell numbers were then determined using a haemocytometer.

Airway smooth muscle cells maintained in culture for 72 hours in the presence of 5% FCS and 2-MEO (10 micro M) underwent a readily discernible shape change (FIG. 4) that was not detected for cells incubated for the same period and at the same concentration of MEG, suggesting that MEG lacked this active of the parent molecule.

Smooth muscle cells were obtained from airways resected from lung transplant recipients and cultured as previously described in detail (Fernandes et al., 1999). Cell numbers were determined in experiments of the same design as those described for human airway fibroblasts with the additional stimulus of 1% (v/v) fetal calf serum (FCS) being evaluated. In addition, [$^3$H]-thymidine incorporation was determined between 24 and 28 hours after the addition of thrombin to determine DNA synthesis (Fernandes et al. 1999).

In human airway fibroblasts thrombin-stimulated increases in cell number were reduced to 12±8% of the control response by 2-MEO, but 2-MEG had no significant effect (Table 1). In human airway smooth muscle responses both thrombin and FCS were reduced to a greater extent by 2-MEO than by 2-MEG. In addition, thrombin-stimulated DNA synthesis was decreased by 2-MEO, but unaffected by 2-MEG (Table 1).

Figure 5:
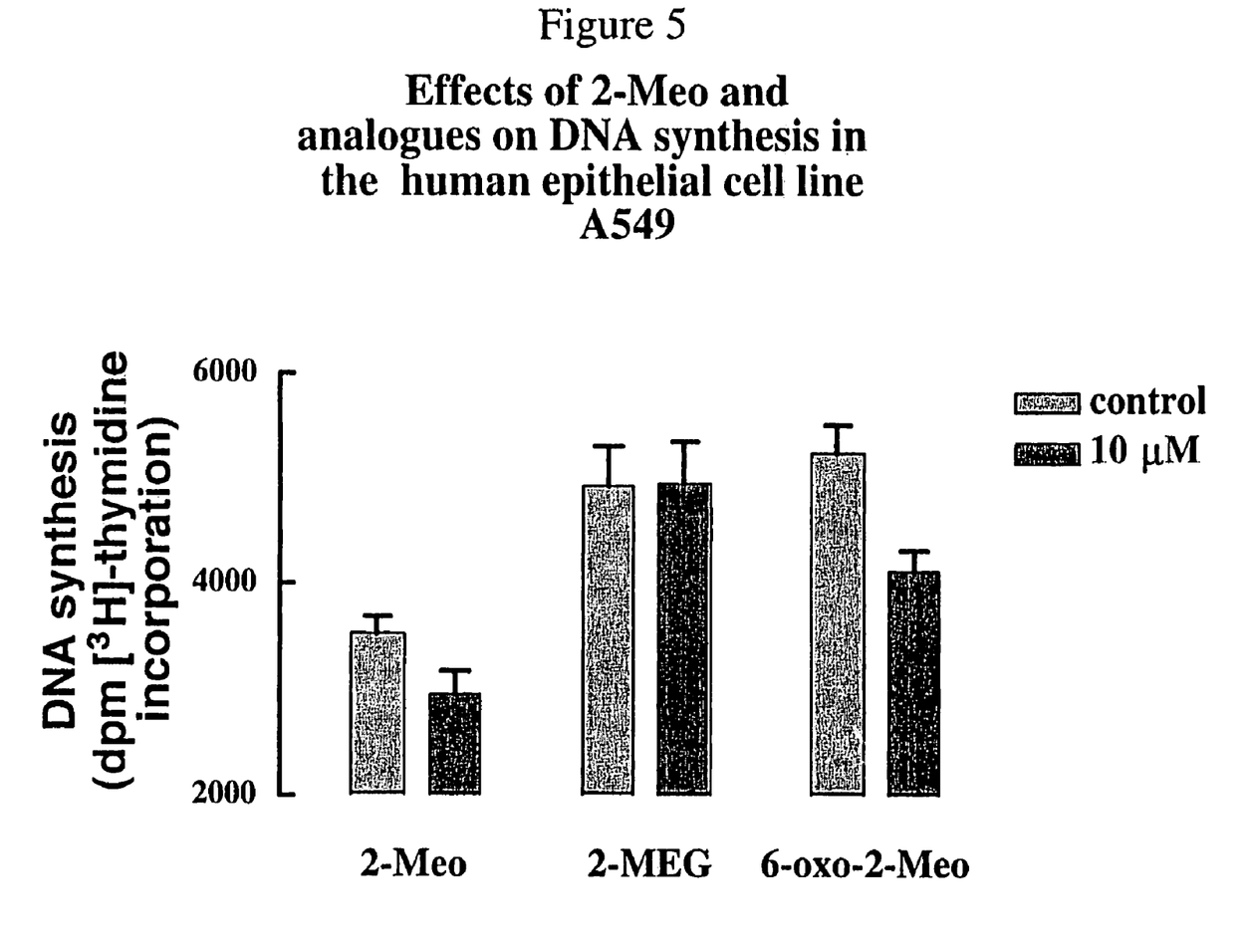

A549 cells were maintained in DMEM containing 5% fetal calf serum and undergoing asynchronous proliferation. DNA synthesis was determined by the addition of [3H]-thymidine 24 hours after the addition of one of 2-methoxyestradiol, 6-oxo-2-methoxyestradiol and 2-methoxyestradiol-17β-D-glucuronide. Both 2-methoxyestradiol and 6-oxo-2-methoxyestradiol at 10 micromolar reduce DNA synthesis significantly whereas 2-methoxyestradiol-17β-D-glucuronide was ineffective (FIG. 5).

These data indicate that 2-MEG is either less active or inactive by comparison with the parent molecule, 2-MEO.

EXAMPLE 6

Rat Uterine Cytosol Estrogen Receptor Binding

Rat uterine cytosiol is a standard preparation of estrogen receptor (Markavevich et al, 19xx). Uteri from four Sprague Dawley rats were pooled, homogenised in 10 ml/g wet weight of buffer (pH 7.4, 0.002 M dithiothreitol, 0.25 M Sucrose) by 3×10s bursts in an ultra Turrax homogeniser. The resulting homogenate was subjected to centrifugation at 1000×g for 5 min at 4° C. to remove nuclei and cellular debris. The supernatant was subjected to centrifugation at 35,000×g for 30 min. at 4° C. in a Beckman JA centrifuge. The supernatant was used in binding assays that were conducted in the same buffer. The displacement of 0.2 nM [$^3$H]estradiol (150 Ci/mmol) was examined by incubating 200 μl of rat uterine cytosol with 50 μL of radioactive estradiol and 50 μL of buffer containing concentrations of estradiol (non-radiolabelled) in the range 0.003 nM to 10 nM; 2-MEO 0.003 to 10 μM; 2-MEG 0.003 to 10 μM. Total binding was determined in incubations in which buffer was added in place of displacing agent and 10 μM estradiol was used to define non-specific binding.

Each of the displacers produced displacement but there was an incomplete response at 10 μM 2-MEO that logIC$_{50}$ values indicate that 2-MEG has only 1/50 the affinity of 2-MEO for estrogen receptors (FIG. 6). It is evident that 2-MEO has significant affinity for estrogen receptors over the concentration range that reduces mesenchymal cell proliferation with a IC$_{50}$ of approximately 100 nM, even though its affinity is considerably less than that of its precursor estradiol (IC$_{50}$ 3 nM).

EXAMPLE 7

Relative Solubilities of 2-MEO and MEG

The octanol:water partition co-efficient is a measure of the relative aqueous and lipid solubility of a compound. For 2-MEO this was determined by fluorescence spectroscopy at Ex=250 nm, Em=325 nm on the aqueous solution after extensive mixing to ensure that an equilibrium had been obtained. The measured octanol/water partition coefficient for 2methoxyestradiol is 9.05 (logP=0.957), and for MEG it is 0.372 (logP=−0.429) using fluorescence spectroscopy at Ex=240 nm, Em=352 nm. Thus, the aqueous solubility of the glucuronide is approximately 25 times that of 2-MEO itself.

TABLE 1

The effects of 2-MEO and MEG on proliferation of human airway fibroblasts or smooth muscle cells measured by DNA synthesis or by increases in cell number.

| Stimulus | 2-MEO (10 μM) | 2-MEG (10 μM) |
|---|---|---|
| Human Airway Fibroblasts Cell Number (% control) | | |
| Thrombin (0.3 U/ml) | 12 ± 8, n = 7 | 123 ± 33, n = 10 |
| Human Airway Smooth Muscle Cell Number (% control) | | |
| Thrombin (0.3 U/ml) | 14 ± 12, n = 10 | 29 ± 8, n = 12 |
| FCS (1%, v/v) | 25 ± 9, n = 5 | 47 ± 16, n = 5 |
| Human Airway Smooth Muscle DNA Synthesis (% control) | | |
| Thrombin (0.3 U/ml) | 24 ± 8, n = 10 | 91 ± 16, n = 4 |

REFERENCES

1. Basta et al., (1999). Modulation of monocytic cell activity and virus susceptibility during differentiation into macrophages. *J. Immunol.*, 162: 3961–3969.
2. Blackwell et al, *Steroids*, 1993, 58, 452–456.
3. Cushman et al, *Journal of Medicinal Chemistry*, 1997, 40, 2323–2334.
4. Fernandes, D. J., Guida, E., Kalafatis, V., Harris, T., Wilson, J. & Stewart, A. G. (1999). Glucocorticoids inhibit proliferation, cyclin D1 expression and retinoblastoma protein phosphorylation, but not mitogen-activated protein kinase activity in human cultured airway smooth muscle. *American Journal of Respiratory Cell Molecular Biology.* 21, 77–88.
5. Fernandes, D., Guida, E., Koutsoubos, V., Harris, T., Vadiveloo, P., Wilson, J. W. & Stewart, A. G. (1999). Glucocorticoids inhibit proliferation, cyclin D1 expression, and retinoblastoma protein phosphorylation, but not activity of the extracellular-regulated kinases in human cultured airway smooth muscle. Am J respir Cell Mol. Biol., 21: 77–88.
6. Fidler, I. J. & Ellis, L. M. (1994). The implications of angiogenesis for the biology and therapy of cancer metastasis. *Cell* 79, 185–188.
7. Franciscus M. H. Journal of Medicinal Chemistry, 2000, 43, 3093–3102.
8. Markaverich, B. M. & Clark, J. H. (1981). Quantitation of nuclear estrogen receptors in the rat uterus by [3H]-estradiol exchange. J. Steroid of Biochemistry, 15: 289–292.

9 Oswald, H., Phelan, P. D., Lanigna, A., Hibbert, M., Bowes, G., & Olinsky, A. (1994). Outcome of childhood asthma in mid-adult life. Brit Med J., 309: 95–96.

10 Zhang S, Howarth P H, Roche W R. (1996). Cytokine production by cell cultures from bronchial subepithelial myofibroblasts. J Pathol. Sep; 180(1):95–101.

Finally, it is to be understood that various alterations, modifications and/or additions may be made without departing from the spirit of the present invention as outlined herein.

It will be understood that the invention disclosed and defined in this specification extends to all alternative combinations of two or more of the individual features mentioned or evident from the text or drawings. All of these different combinations constitute various alternative aspects of the invention.

It will also be understood that the term "comprises" (or its grammatical variants) as used in this specification is equivalent to the term "includes" and should not be taken as excluding the presence of other elements or features.

The invention claimed is:

1. A pharmaceutical composition comprising:
   a conjugated prodrug of an estradiol compound conjugated to a sugar moiety, wherein the sugar moiety is a glucuronide and the estradiol compound is selected from the group consisting of 6-oxo-2-methoxyestradiol; 3-acetyl-6-oxo-2-methoxyestradiol; and 2-methoxyestradiol-6-hydrazone and a pharmaceutically acceptable carrier, diluent or excipient therefor.

2. The pharmaceutical composition of claim 1, wherein the glucuronide is conjugated at positions 3 and/or 17 of the estradiol compound.

* * * * *